United States Patent [19]

Martin et al.

[11] 4,211,784
[45] Jul. 8, 1980

[54] BIS(DITHIOCARBAMATE) SALTS

[75] Inventors: Charles W. Martin, Lake Jackson; Eldon L. Ward, Angleton, both of Tex.

[73] Assignee: The Dow Chemical Company, Midland, Mich.

[21] Appl. No.: 41,160

[22] Filed: May 21, 1979

Related U.S. Application Data

[62] Division of Ser. No. 951,915, Oct. 16, 1978.

[51] Int. Cl.$^2$ .................. A01N 9/12; C07C 155/08
[52] U.S. Cl. .................. 424/267; 260/455 A; 424/286; 546/8
[58] Field of Search .................. 260/455 A; 424/286, 424/267; 546/8

[56] References Cited

U.S. PATENT DOCUMENTS 3,517,040   6/1970   Lewis et al. .................. 546/8

*Primary Examiner*—Alan L. Rotman
*Assistant Examiner*—Robert C. Whittenbaugh

[57] ABSTRACT

Novel bis(dithiocarbamate) salts, the mixed transition metal salts, and zinc salt amine complexes thereof are claimed. These novel compounds have utility as antifungal agents.

8 Claims, No Drawings

BIS(DITHIOCARBAMATE) SALTS

This is a Divisional of Application Ser. No. 951,915, filed Oct. 16, 1978.

SUMMARY OF THE INVENTION

This invention is directed to novel bis(dithiocarbamate) salts, the mixed transition metal salts and zinc salt amine complexes thereof, all of which hereinafter alternatively referred to as "active compounds", and to a method and composition employing the same. The active compounds of the present invention are useful as antifungal agents.

The invention's novel bis(dithiocarbamate) salts, correspond to the formula

wherein n is the valence of M and is 1, 2, or 3, and M is ammonium, an alkali metal, or a transition metal. The ammonium and alkali metal salts are water soluble and the transition metal salts are water insoluble.

This invention is also concerned with novel mixed transition metal bis(dithiocarbamate) salts that correspond to the formula

wherein X and Y are not the same and represent a bivalent transition metal cation and $a+b=1$, with the proviso that a and b are, individually, greater than 0.

This invention is further concerned with novel zinc salt amine complexes of the formula

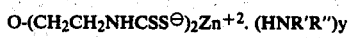

wherein R' and R" are, individually, either $CH_2CH_2NH_2$ or $CH_2CH_2OH$, or R' and R", taken together, is $-(CH_2)_5-$; and y has a value of from about 0.10 to about 2.

The term "alkali metal" is employed in the present specification and claims to designate Li, Na and K. The term "transition metal" is employed in the present specification and claims to designate Zn, Mn, Cu, Co, Fe and Ni.

The novel water-soluble salts of the present invention, i.e., the alkali metal and ammonium salts, are prepared by reacting bis(2-aminoethyl)ether, carbon disulfide and the corresponding aqueous alkali metal hydroxide or ammonium hydroxide. The reaction mixture is maintained at about 25° C. to about 30° C., with agitation, during addition of the $CS_2$ over a period of about one hour. The mixture is then heated at approximately 35° C. for about one hour to ensure substantial completion of the reaction. The product compound is recovered and purified by conventional techniques known to those in the art.

In the above reaction, the preferred molar ratio of both carbon disulfide and the hydroxide starting material to the ether starting material is approximately 2:1. It is understood, however, that either the carbon disulfide or the hydroxide starting material may be employed in amounts that are in excess of the preferred molar amounts as set forth above.

The novel water-insoluble salts of the present invention, i.e., the transition metal salts, are prepared by reacting, in water, a transition metal salt such as the sulfate or chloride with water-soluble salt of the present invention, as formed by the above-detailed procedure. The reaction mixture is stirred at room temperature until substantial completion of the reaction, usually from about 10 to about 30 minutes. The product compound is recovered and purified by conventional techniques known to those in the art.

The preferred molar ratio of the metal salt starting material to the water-soluble salt starting material is 2/n:1, wherein n is the valence of the free transition metal cation. The metal salt starting material may, however, be used in excess of of the preferred molar ratios as calculated by the above procedure.

The mixed transition metal salts of the present invention are prepared from the corresponding transition metal salts. In the process, both of the corresponding transition metal salts are dissolved in water and the resulting solution is added to an aqueous solution of a water-soluble salt of the present invention. The thus-formed reaction mixture is stirred at room temperature (~25° C.) until substantial completion of the reaction, usually from about 10 to about 30 minutes. The product compound is recovered and purified by conventional techniques known to those in the art.

In the above process for preparing mixed transition metal salts, the preferred molar ratio of the combined moles of the transition metal salt employed to the moles of water-soluble salt starting material employed is 1:1. However, combined transition metal salt in excess of the preferred amount may be employed. Those skilled in the art will readily understand that the molar ratio of the transition metal cations to each other in the mixed salt product will be determined by the molar ratio, in the above-described process, of the transition metal salts to each other. Thus, for example, if a $Zn_{0.50}Mo_{0.50}$ mixed salt is desired, the molar ratio of the Zn salt starting material to the Mn salt starting material will be 1:1.

The novel zinc salt amine complexes of the present invention are prepared by reacting, in water, a zinc salt, such as the sulfate, a water-soluble salt of the present invention and a secondary amine. Amines of the formula HNR'R", wherein R' and R" are defined as set forth above, are particularly suitable. The resulting reaction mixture is stirred at room temperature until substantial completion of the reaction, usually from about 0.1 to about 4 hours. The product compound is recovered and purified by conventional techniques known to those in the art.

In the above reaction, the preferred molar ratio of the zinc salt starting material to the water-soluble salt starting material is 1:1. The molar ratio, in the above reaction, of the amine starting material to the water-soluble salt starting material will determine the amine/zinc salt molar ratio in the resulting complex. The molar ratio of the water-soluble salt to the amine starting material will range from about 1:0.1 to about 1:2.

In accordance with the present invention, useful compositions related structurally to those specifically disclosed herein may be prepared by treating the water-soluble salts of the present invention with oxidizing agents such as, for example, hydrogen peroxide.

DESCRIPTION OF THE PREFERRED EMBODIMENTS

The following examples and teachings illustrate the present invention and the manner by which it can be practiced but as such should not be construed as limitations upon the overall scope of the same. The product compounds are identified by infrared spectroscopy and elemental analysis.

EXAMPLE 1

Preparation of diammonium (oxydi-2,1-ethanediyl)biscarbamodithioate (Compound 1)

To a solution of 52.0 g (0.5 mole) of bis(2-aminoethyl)ether, 60.0 g (1 mole) of conc. $NH_4OH$ and 175 ml of water was added, with stirring, 76 g (1 mole) of carbon disulfide over a period of 1¼ hours. External cooling was applied to the reaction vessel during the addition of the $CS_2$ to control the resulting exothermic reaction at 25°–31° C. After the addition of the $CS_2$ was completed, the contents of the reaction vessel were heated at 37° C. for 1½ hours and then cooled to ambient temperature. The resultant clear orange liquid slowly changed to a brilliant yellow solution upon standing overnight in a closed bottle. The solution contained about 40.0 weight percent diammonium(oxydi-2,1-ethanediyl)biscarbamodithioate:

$O-(CH_2CH_2NHCSS^{\ominus})_2 2NH_4^{\oplus}$

EXAMPLE 2

Preparation of disodium(oxydi-2,1-ethanediyl)biscarbamodithioate (Compound 2)

The procedure of Example 1 was repeated with the exception that NaOH was substituted for $NH_4OH$ in the reaction. In this example, 60.9 g (0.80 mole) of $CS_2$ was added, with stirring, to a solution of 41.60 g (0.4 mole) of bis(2-aminoethyl)ether, 32.5 g (0.8 mole) of 98.5 percent NaOH pellets over a period of 1¼ hours at a temperature of 28°–35° C. The reaction temperature was maintained at 35° C. for an additional hour after the $CS_2$ addition was completed. The orange reactant solution contained about 30.0 weight percent disodium(oxydi-2,1-ethanediyl)biscarbamodithioate:

$O-(CH_2CH_2NHCSS^{\ominus})_2 2Na^{\oplus}$

EXAMPLE 3

Preparation of Zinc(oxydi-2,1-ethanediyl)biscarbamodithioate (Compound 3)

To a solution of 500 ml of water and 50.0 g (0.069 mole of Compound 1) of the reaction solution from Example 1 was added, with stirring, 19.84 g (0.069 mole) of $ZnSO_4.7H_2O$ in 50 ml $H_2O$ over a period of 10 minutes at 25° C. A finely dispersed white precipitate began to form immediately upon the addition of the aqueous zinc sulfate solution. The mixture was stirred an additional 30 minutes whereupon the resulting precipitate was collected by filtration. The filter cake was washed twice with water, once with methanol, and allowed to air dry overnight under a constant flow of air, yielding 20.45 g of zinc(oxydi-2,1-ethanediyl)biscarbamodithioate:

$O-(CH_2CH_2NHCSS^{\ominus})_2 Zn^{2+}$ as a fine white powder. The yield, based on the bis(2-aminoethyl)ether, was 81.1 weight percent of theory. Infrared analysis confirmed the proposed structure.

EXAMPLE 4

Preparation of Manganese (oxydi-2,1-ethanediyl)biscarbamodithioate (Compound 4)

Following the procedure set forth in Example 3, but substituting an aqueous solution of manganese sulfate for zinc sulfate, the following compound was obtained as a brown powder:

$O-(CH_2CH_2NHCSS^{\ominus})_2 Mn^{2+}$

EXAMPLE 5

Preparation of the $Zn_{0.95}^{+2}/Mn_{0.05}^{+2}$ mixed salt of (oxydi-2,1-ethanediyl)biscarbamodithioate (Compound 5)

To a solution of 10.15 g (0.0351 mole) of Compound 1 in 200 ml $H_2O$ was added, with stirring and over a period of 30 minutes, a solution of 9.67 g (0.336 mole) $ZnSO_4.7H_2O$ and 0.30 g (0.018 mole) $MnSO_4.7H_2O$ dissolved in 25 ml $H_2O$. The resulting precipitate was filtered, washed once with water and once with methanol, and dried under vacuum in a dessicator for 7 hours, to yield 10.8 g (96.5 percent of theory, calculated from Compound 1) of the titled compound as a fine purple powder.

Following the procedure of Example 5, but using the appropriate molar ratio of zinc sulfate/manganese sulfate, the following $Zn^{+2}/Mn^{+2}$ mixed salts of (oxydi-2,1-ethanediyl)biscarbamodithioate were prepared. The product compounds were identified by elemental analysis, and infrared analysis:

EXAMPLE 6

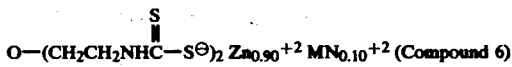

$$O-(CH_2CH_2NH\overset{S}{\overset{\|}{C}}-S^{\ominus})_2 \ Zn_{0.90}^{+2} \ Mn_{0.10}^{+2} \ \text{(Compound 6)}$$

EXAMPLE 7

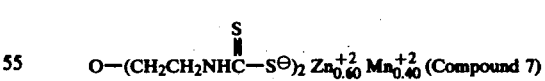

$$O-(CH_2CH_2NH\overset{S}{\overset{\|}{C}}-S^{\ominus})_2 \ Zn_{0.60}^{+2} \ Mn_{0.40}^{+2} \ \text{(Compound 7)}$$

EXAMPLE 8

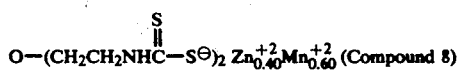

$$O-(CH_2CH_2NH\overset{S}{\overset{\|}{C}}-S^{\ominus})_2 \ Zn_{0.40}^{+2} Mn_{0.60}^{+2} \ \text{(Compound 8)}$$

EXAMPLE 9

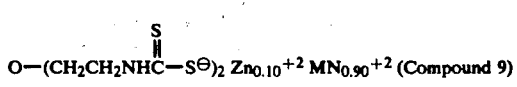

$$O-(CH_2CH_2NH\overset{S}{\overset{\|}{C}}-S^{\ominus})_2 \ Zn_{0.10}^{+2} \ Mn_{0.90}^{+2} \ \text{(Compound 9)}$$

EXAMPLE 10

Preparation of (oxydi-2,1-ethanediyl)biscarbamodithioate (2-)copper (Compound 10)

To a solution of 41.62 g of $CuSO_4 \cdot 5H_2O$ (0.166 mole) in 400 ml $H_2O$ was added, with stirring, 100 g (0.0833 mole) of a 25 percent aqueous solution of Compound 2 over a period of 30 minutes at 25° C. The reaction mixture was stirred for an additional 30 minutes at 25° C. and filtered. The resulting precipitate was washed once with water, twice with water and dried for 3 hours under vacuum at 38° C. to yield 27.72 g of the desired product as a green powder, m.p. 150°–155° C. (decomposition). Infrared analysis confirmed the assigned structure:

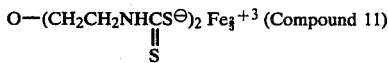

EXAMPLE 11

Following the procedure of Example 10, the $Fe^{+3}$ salt of (oxydi-2,1-ethanediyl)biscarbamodithioate was prepared by substituting 9.0 g (0.0416 mole) of $FeCl_3$ for the $CuSO_4$ utilized in Example 10. There was obtained 21.2 g (87.3 percent yield) of the desired compound as a black powder, m.p. 93°–125° C. (decomposition). Infrared analysis confirmed the assigned structure:

$$O-(CH_2CH_2NHCS^\ominus)_2 \underset{\underset{S}{\|}}{Fe_{\frac{2}{3}}^{+3}} \text{ (Compound 11)}$$

EXAMPLE 12

In this Example a zinc salt amine complex of the present invention was prepared as follows:

To a 39.52% solution (1700 g, 2.3 moles) of compound 1 diluted in five liters of water was added, with stirring and over a period of 3 hours, 65 g (2.3 moles) of $Zn SO_4 \cdot 7H_2O$ in 2 liters of water and 60.1 g (0.58 moles) of (2-(2-aminoethyl)amino)ethanol ($H_2NCH_2CH_2NHCH_2CH_2OH$) in 1 liter of water. The thus-formed white slurry was vacuum filtered, and the precipitate was washed twice with water, once with methanol, and once with acetone to yield 787.5 g (98.5% of theory, calculated from Compound 1) of the following complex as a white powder:

O-(CH_2CH_2NHCSS^⊖)_2Zn^{+2}·(H_2NCH_2CH_2NHCH_2CH_2OH)_{0.25} (Compound 12)

EXAMPLE 13

Following the procedure of Example 12, and using a Compound 1/amine molar ratio of 1:1, the following complex was prepared as a white powder:

O-(CH_2CH_2NHCSS^⊖)_2Zn^{+2}·H_2NCH_2CH_2NHCH_2CH_2OH (Compound 13)

EXAMPLE 14

Following the procedure of Example 12, but substituting piperdine for (2-(2-aminoethyl)amino)ethanol and using a Compound 1/amine molar ratio of 1:1, the following complex was prepared as a white powder:

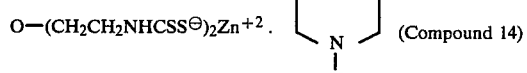

EXAMPLE 15

Following the procedure of Example 14, and using a Compound 1/amine molar ratio of 1:2, the following complex was prepared as a white powder:

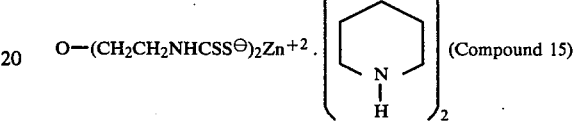

EXAMPLE 16

Following the procedure of Example 14, and using a Compound 1/amine molar ratio of 2:1, the following complex was prepared as a white powder:

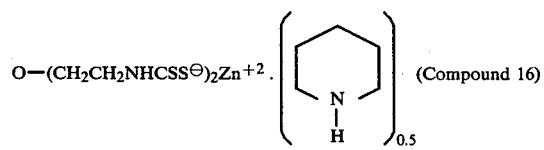

The active compounds of the present invention can be employed to control plant fungus attack. In such operations, the active compounds are employed by contacting fungi and their habitat with an antifungal amount of one or more of the active compounds, the term "habitat" here being used in its broadest sense to include higher plants and plant parts thereof, growth media and any other spaces, areas or surfaces with which fungi may come into contact. The term "higher plant" includes the chlorophyllous plants having leaves, stems, roots and the like such as the angiospermae and gymnospermae. In addition, the active compounds are advantageously employed to control fungal attack on such representative higher plants are almond, apple, apricot, banana, cherry, peach, pear, grape, carrot, tomato, cabbage, cucumber, cantalope, spinach, potato, beet, corn, hops, rice, wheat, beans, cotton, lettuce, onions, celery, tobacco and other crop plants as well as ornamental shrubs and flowering plants and turf grasses. Excellent control of plant fungi is observed when the active compounds are applied to the above-ground portions of higher plants in antifungal amounts from about 0.1 pounds to about 10 pounds of active compound per acre. Similarly, application of active compounds to seeds of higher plants in antifungal amounts of from about 1 ounce to about 48 ounces of active compound per 100 pounds of seed provides excellent control of plant fungi without inhibiting germination of the seed and growth of plants therefrom.

The active compounds can be employed in their unmodified form or they can be employed in compositions comprising additaments and adjuvants, preferably a non-phytotoxic adjuvant. The term "non-phytotoxic adjuvant" refers to conventional fungicide adjuvants which are not substantially deleterious to plant leaves, stems, flowers, fruit and the like and not substantially inhibitory to the growth of plants are rates of application of active compounds consistent with good antifungal activity. Such compositions can contain from about 5 to about 95 percent by weight of an active compound. Dust compositions can be formulated by employing finely divided solid adjuvants such as powdered walnut shells, pyrophyllite, chalk, talc, gypsum or the like and can include solid surface active dispersing agents such as fuller's earth, bentonite, montmorillonite, kieselguhr, attapulgite clay and the like. The compositions can also be prepared as concentrate compositions containing from about 50 to about 95 percent of an active compound. Such compositions are adapted to be diluted by admixture with additional adjuvants prior to use.

The compositions can also be formulated as wettable powders including ionic or nonionic surface active dispersing agents. A preferred group of compositions includes those comprising an active compound and a surface active dispersing agent. The term "surface active dispersing agent" is employed herein to include all agents which are capable of acting as the interfacial surface between the active compounds and water or an organic liquid as the dispersion medium, facilitating thereby the dispersion of the active compound in water or organic liquid to form dispersible concentrate compositions or the like. Representative surface active dispersing agents include bentonite, montmorillonite, fuller's earth, attapulgite and other clays, condensation products of alkylene oxides with phenols and organic acids, alkyl aryl sulfonates, fatty acid esters of sugars and ethylene oxide derivatives thereof, polyoxyethylene derivatives or sorbitan esters, complex alcohols, mahogany soaps and the like. Particularly good results can be obtained by the use of lignin sulfonates such as the calcium, magnesium, sodium or potassium salts or by the use of goulac which is a mixture of magnesium lignin sulfonate, calcium lignin sulfonate and pentose sugars, these lignin additives can be employed alone or along with non-phytotoxic polyvalent metal ion-containing compounds (e.g., sulfates, sulfites or chlorides of iron or zinc) as well as with other wetting and dispersing agents and with dispersion stabilizers, as recited below. Other suitable surface active dispersing agents can be found in "Detergents and Emulsifiers, Up to Date" written and published by John W. McCutcheon, Inc., Morristown, New Jersey, 1967.

The preferred compositions comprising an active compound and a surface active dispersing agent can be treating compositions containing from about 5 or less to about 95 or more percent by weight of the active compound, or they can be concentrate compositions containing from about 50 to about 95 percent by weight of the active compound. These concentrate compositions can be diluted by the addition of additaments, non-phytotoxic adjuvants and the like to prepare the ultimate treating compositions.

The active compounds can also be incorporated with other active agents to provide combinations of effects in particular operations. For example, the compositions can include additional fungicides or preservatives such as the phenolic preservatives, halogenated salicylanilides, sulfur, copper fungicides and the like; insecticides, nematocides, and other pesticides such as malathion, karathane, 0,0-diethyl-0-p-nitrophenylthiophosphate, methyl bromide, ethylene dibromide, 0,0-diethyl-0-(3,5,6-trichloro-2-pyridyl)phosphate and the like; fertilizers including ammonium, phosphate and urea fertilizers and trace mineral plant nutrients, and preemergent or post-emergent herbicides such as the halogenated phenoxy aliphatic acids, dinitro-secondary-butylphenol, 3-(3,4-dichlorophenyl)-1,1-dimethylurea and the like. When the active compounds are employed to treat higher plants, any other active agents are selected to provide a composition which will provide the desired additional effects such as control of other fungi, insects, slugs, nematodes and weeds without adversely affecting the plant species treated.

The active compounds and compositions containing the same can be applied to plants, fungi or growth media by conventional procedures including spraying, dipping, dusting, rolling onto plant seeds, application to soil with or without subsequent incorporation by dusting or the like, impregnation, dispersion in irrigation water or the like. The compositions can be applied at rates varying from a few pounds or gallons to several hundred pounds or gallons per acre, depending upon such factors as the particular active compound employed, the concentration of active compound and the effect to be produced, so long as plants, plant parts or their habitats are contacted with an antifungal amount of an active compound.

In addition, incorporation of the active compounds of this invention into materials which are subject to fungal attack inhibits the growth of the fungi and preserves the original value of the materials. Examples of materials which are adversely affected by fungal growth are latex and alkyl paint films, wood and wooden products. The active compounds are therefore useful for long-term protection against fungal growth in or on materials subject to fungal attack.

For such uses, the active compounds can be employed in an unmodified form or dispersed on a finely divided solid and employed as a dust. Such mixtures can also be dispersed in water with the aid of a surface-active agent and the resulting emulsion employed as a spray. The augmented compositions are adapted to be formulated as concentrates and subsequently diluted with additional solid adjuvants to produce the ultimate treating compositions. Good control and kill have been realized against a number of representative organisms with compositions wherein antifungally-effective amounts of from about 1 to about 500 parts by weight of one or more of the active compounds per million parts of such compositions are employed. As stated hereinbefore, the active antifungal amount to be employed against a given organism or in a certain composition can readily be determined by one skilled in the art.

In representative tests for antifungal activity, samples of each of Compounds 1 through 4 were individually dispersed in warm melted nutrient agar which was poured into Petri dishes and allowed to solidify, the active compounds being employed in an amount sufficient to provide from 1 to 500 parts by weight thereof per million parts (ppm) of the ultimate agar composition. The surfaces of the agar was inoculated with a variety of fungal pest organisms, and the inoculated plates incubated under conditions conductive to fungal growth. Similar check plates in which the agar did not contain the active compounds or other toxic compounds were similarly inoculated and incubated.

In these studies, Compounds 1 through 4 gave 100 percent growth inhibition (kill) and control of the following organisms, as set forth in Table I, at the indicated concentrations in parts per million (ppm):

TABLE I

ANTIMICROBIAL ACTIVITY

| Organism | Minimum Inhibiting Concentration in ppm | | | |
|---|---|---|---|---|
| | Compound 1 | Compound 2 | Compound 3 | Compound 4 |
| P. Chrysogenum | 10 | 50 | 5 | 50 |
| A. Niger | 50 | 100 | 5 | 50 |
| C. Pelliculosa | 10 | 50 | 10 | 50 |
| A. Pullularia Pullulans | 10 | 500 | 10 | 50 |
| C. Ips | 50 | 50 | 5 | 50 |
| Trichoderm Sp. P-42 | 50 | 500 | 50 | 500 |

In representative in vivo operations, Compound 1, when employed as the sole toxicant at a concentration of 400 parts by weight per million parts (ppm) of the ultimate composition was found to give, individually, 90 percent kill and control of grape downy mildew (*Plasmopara viticola*) and 95 percent kill and control of apple scab (*Venturia inaequalis*) and, at a concentration of 25 ppm, was found to give 100 percent kill and control of tobacco black shank (*Phytophthora parasitica* var. *nicotianae*).

In further representative in vivo operations, Compound 3 was found to give 100 percent kill and control of grape downy mildew when employed at a concentration of 400 ppm and 95 percent kill and control of wheat leaf rust (*Ruccinia recondita*) when employed at a concentration of 100 ppm. In similar operations, Compound 4 gave 99 percent kill and control of apple scab when employed at a concentration of 400 ppm; Compound 5 gave, individually, 90 percent and 99 percent kill and control of, respectively, apple scab and wheat leaf rust when employed at a concentration of 500 ppm, 97 percent kill and control of grape downy mildew when applied at a concentration of 400 ppm, and 100 percent control and kill tobacco black root rot (*Thielaviopis basicola*) when employed at a concentration of 25 ppm.

In additional representative in vivo operations, Compounds 6, 7, 12, 13, 15 and 16 gave the following percent control and kill, as set forth in the Table below, against the indicated organisms when employed at a concentration of 400 ppm.

TABLE (Figures indicate percent control and kill at 400 ppm)

| Compound | Organism | | |
|---|---|---|---|
| | GDM | RB | WLR |
| 6 | 93 | 0 | 90 |
| 7 | 50 | 50 | 90 |
| 12 | 100 | 90 | 90 |
| 13 | 83 | 50 | 0 |
| 15 | 100 | 83 | 93 |
| 16 | 97 | 95 | 90 |

GDM = grape downy mildew
RB = rice blast (*piricularia orzae*)
WLR = wheat leaf rust

What is claimed is:

1. A zinc amine complex of the formula $$O-(CH_2CH_2NHCSS^\ominus)_2Zn^{+2}\cdot(HNR'R'')_y$$

wherein R' and R'' are, individually, either $CH_2CH_2NH_2$ or $CH_2CH_2OH$ and R' and R'', taken together, is $-(CH_2)_5-$; and y has a value of from about 0.10 to about 2.

2. The compound of claim 1 which has the formula $$O-(CH_2CH_2NHCSS^\ominus)_2Zn^{+2}\cdot(H_2NCH_2CH_2NHCH_2CH_2OH)_{0.25}.$$

3. The compound of claim 1 which has the formula
$$O-(CH_2CH_2NHCSS^\ominus)_2Zn^{+2}\cdot H_2NCH_2CH_2NHCH_2CH_2OH.$$

4. The compound of claim 1 which has the formula

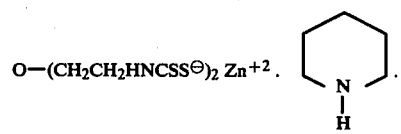

5. The compound of claim 1 which has the formula

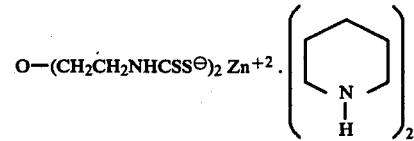

6. The compound of claim 1 which has the formula

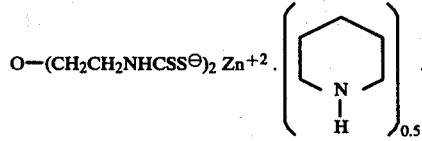

7. A method for controlling fungi which comprises applying to said fungi or their habitat an antifungal amount of a compound of claim 1.

8. A composition for controlling fungi comprising an antifungal amount of a compound of claim 1 in combination with a solid or liquid diluent medium.